(12) United States Patent
Hall

(10) Patent No.: US 11,628,055 B2
(45) Date of Patent: Apr. 18, 2023

(54) METHODS OF MANUFACTURING AN EMBOLIC FILTER BALLOON

(71) Applicant: Merit Medical Systems, Inc., South Jordan, UT (US)

(72) Inventor: John William Hall, North Salt Lake, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 531 days.

(21) Appl. No.: 16/447,752

(22) Filed: Jun. 20, 2019

(65) Prior Publication Data
US 2019/0307543 A1    Oct. 10, 2019

Related U.S. Application Data

(63) Continuation of application No. 14/198,757, filed on Mar. 6, 2014, now abandoned.
(Continued)

(51) Int. Cl.
*B29C 65/02*    (2006.01)
*B29C 65/48*    (2006.01)
(Continued)

(52) U.S. Cl.
CPC ............. *A61F 2/013* (2013.01); *A61M 25/10* (2013.01); *A61M 25/1011* (2013.01);
(Continued)

(58) Field of Classification Search
CPC ......... B29C 65/02; B29C 65/48; B29C 65/62; B29C 66/72; B29C 66/723; B29C 66/729; B29C 70/68; B29K 2027/18; B29L 2031/14; B29L 2031/7543; B32B 37/16; D01D 1/02; D01D 5/12; D01D 5/18;
(Continued)

(56) References Cited

U.S. PATENT DOCUMENTS

| 4,447,227 A | 5/1984 | Kotsanis |
| 4,576,142 A | 3/1986 | Schiff |

(Continued)

FOREIGN PATENT DOCUMENTS

| CA | 2633578 | 9/2008 |
| EP | 1578850 | 9/2005 |

(Continued)

OTHER PUBLICATIONS

Office Action dated Sep. 16, 2020 for U.S. Appl. No. 14/864,361.
(Continued)

*Primary Examiner* — Leo B Tentoni
(74) *Attorney, Agent, or Firm* — Dorsey & Whitney LLP

(57) ABSTRACT

An embolic filter balloon is disclosed. The embolic filter balloon may comprise an inflatable balloon portion. Further, the inflatable balloon portion may be coupled to a filter member. The embolic filter balloon may be disposed in a body lumen. In some embodiments, the embolic filter balloon may be configured such that when the inflatable balloon portion is at least partially inflated the filter member extends at least partially across the body lumen. Such a configuration may allow the embolic filter balloon, when deployed, to filter particles greater than a predetermined size from a fluid in the body lumen.

15 Claims, 10 Drawing Sheets

Related U.S. Application Data

(60) Provisional application No. 61/773,999, filed on Mar. 7, 2013.

(51) Int. Cl.

| | |
|---|---|
| *B29C 65/62* | (2006.01) |
| *B29C 70/68* | (2006.01) |
| *B32B 37/16* | (2006.01) |
| *D01D 1/02* | (2006.01) |
| *D01D 5/12* | (2006.01) |
| *D01D 5/18* | (2006.01) |
| *D01D 11/06* | (2006.01) |
| *D02J 1/22* | (2006.01) |
| *A61F 2/01* | (2006.01) |
| *D01D 5/00* | (2006.01) |
| *D01F 6/12* | (2006.01) |
| *B29C 65/00* | (2006.01) |
| *A61M 25/10* | (2013.01) |
| *B29K 27/18* | (2006.01) |
| *B29L 31/00* | (2006.01) |
| *B29L 31/14* | (2006.01) |

(52) U.S. Cl.
CPC ............ *B29C 66/72* (2013.01); *B29C 66/723* (2013.01); *B29C 66/729* (2013.01); *D01D 5/003* (2013.01); *D01F 6/12* (2013.01); *A61F 2/011* (2020.05); *A61F 2002/016* (2013.01); *A61F 2210/0076* (2013.01); *A61F 2230/0006* (2013.01); *A61F 2230/0069* (2013.01); *A61F 2230/0076* (2013.01); *A61F 2240/001* (2013.01); *A61F 2250/0003* (2013.01); *A61M 25/1002* (2013.01); *A61M 2025/109* (2013.01); *A61M 2025/1097* (2013.01); *A61M 2207/00* (2013.01); *B29K 2027/18* (2013.01); *B29L 2031/14* (2013.01); *B29L 2031/7543* (2013.01); *D10B 2331/042* (2013.01); *D10B 2401/10* (2013.01); *D10B 2505/04* (2013.01)

(58) Field of Classification Search
CPC ... D01D 11/06; D01F 6/12; D02J 1/22; D10B 2331/042; D10B 2401/10; D10B 2505/04
USPC .... 264/129, 210.8, 211.1, 234, 258, 331.14; 156/242, 244.11, 244.24, 293
See application file for complete search history.

(56) References Cited

U.S. PATENT DOCUMENTS

| | | | |
|---|---|---|---|
| 4,662,885 A | 5/1987 | Dipisa, Jr. | |
| 5,108,370 A | 4/1992 | Walinsky | |
| 5,470,314 A | 11/1995 | Walinsky | |
| 5,512,051 A | 4/1996 | Wang et al. | |
| 5,662,960 A | 9/1997 | Hostettler et al. | |
| 5,968,068 A | 10/1999 | Dendashtian et al. | |
| 6,033,379 A | 3/2000 | Barra et al. | |
| 6,090,097 A | 7/2000 | Barbut | |
| 6,139,517 A | 10/2000 | Macoviak | |
| 6,143,014 A | 11/2000 | Dehdashtian et al. | |
| 6,270,902 B1 | 8/2001 | Tedeschi et al. | |
| 6,398,758 B1 | 6/2002 | Jacobsen et al. | |
| 6,491,712 B1 | 12/2002 | O'Connor | |
| 6,558,405 B1 | 5/2003 | McInnes | |
| 2002/0010411 A1 | 1/2002 | Macoviak | |
| 2002/0045049 A1 | 4/2002 | Madsen | |
| 2002/0068180 A1 | 6/2002 | Yang et al. | |
| 2002/0087123 A1* | 7/2002 | Hossainy | A61L 31/16 427/2.24 |
| 2002/0128680 A1 | 9/2002 | Pavlovic | |
| 2002/0165521 A1 | 11/2002 | Cioanta et al. | |
| 2002/0165523 A1 | 11/2002 | Chin et al. | |
| 2003/0018353 A1 | 1/2003 | Yang et al. | |
| 2003/0065355 A1* | 4/2003 | Weber | A61L 29/126 606/200 |
| 2003/0176886 A1 | 9/2003 | Wholey et al. | |
| 2003/0208224 A1* | 11/2003 | Broome | A61F 2/0108 606/200 |
| 2004/0015052 A1 | 1/2004 | Barthel | |
| 2004/0148007 A1 | 7/2004 | Jackson et al. | |
| 2005/0004597 A1 | 1/2005 | McGuckin, Jr. | |
| 2005/0055044 A1 | 3/2005 | Kangas | |
| 2005/0159771 A1* | 7/2005 | Petersen | A61F 2/0105 606/159 |
| 2005/0234501 A1 | 10/2005 | Barone | |
| 2006/0015136 A1 | 1/2006 | Besselink | |
| 2006/0100662 A1 | 5/2006 | Daniel et al. | |
| 2007/0112300 A1 | 5/2007 | Roman et al. | |
| 2007/0129748 A1 | 6/2007 | Eidenschink et al. | |
| 2007/0167973 A1 | 7/2007 | Stupecky et al. | |
| 2008/0152635 A1 | 6/2008 | Lee et al. | |
| 2009/0227944 A1 | 9/2009 | Weber | |
| 2009/0280325 A1 | 11/2009 | Lozano et al. | |
| 2009/0312807 A1 | 12/2009 | Boudreault et al. | |
| 2010/0217186 A1 | 8/2010 | Nazarova et al. | |
| 2010/0312268 A1 | 12/2010 | Belson | |
| 2011/0152918 A1 | 6/2011 | Chin | |
| 2012/0016408 A1 | 1/2012 | Barbut et al. | |
| 2012/0035635 A1 | 2/2012 | Weber et al. | |
| 2012/0109179 A1 | 5/2012 | Murphy | |
| 2012/0109182 A1 | 5/2012 | Belson | |
| 2012/0114722 A1* | 5/2012 | Ballard | D01F 6/12 977/788 |
| 2012/0197380 A1 | 8/2012 | Holman et al. | |
| 2012/0292795 A1 | 11/2012 | Peno et al. | |
| 2013/0006175 A1 | 1/2013 | Elton | |
| 2014/0035177 A1* | 2/2014 | Lipton | D01D 5/18 264/8 |
| 2014/0086971 A1* | 3/2014 | Hall | D01D 5/18 514/56 |
| 2014/0193474 A1 | 7/2014 | Babcock et al. | |
| 2015/0118565 A1* | 4/2015 | Bell | H01M 4/525 429/246 |
| 2015/0250577 A1 | 9/2015 | Hall | |
| 2015/0272732 A1 | 10/2015 | Tilson et al. | |
| 2018/0360586 A9 | 12/2018 | Hall et al. | |
| 2021/0128333 A1 | 5/2021 | Hopkinson et al. | |

FOREIGN PATENT DOCUMENTS

| | | |
|---|---|---|
| WO | 199810713 | 3/1998 |
| WO | 2014138404 | 9/2014 |

OTHER PUBLICATIONS

International Search Report and Written Opinion dated Jan. 5, 2016 for PCT/US2015/051842.
International Search Report and Written Opinion dated Jul. 1, 2014 for PCT/US2014/021220.
Office Action dated Jan. 9, 2018 for U.S. Appl. No. 14/198,757.
Office Action dated Feb. 21, 2019 for U.S. Appl. No. 14/198,757.
Office Action dated Feb. 21, 2019 for U.S. Appl. No. 14/864,361.
Office Action dated Mar. 9, 2017 for U.S. Appl. No. 14/198,757.
Office Action dated Mar. 24, 2016 for U.S. Appl. No. 14/198,757.
Office Action dated Jun. 21, 2018 for U.S. Appl. No. 14/198,757.
Office Action dated Jul. 3, 2017 for U.S. Appl. No. 14/198,757.
Office Action dated Jul. 24, 2018 for U.S. Appl. No. 14/864,361.
Office Action dated Aug. 12, 2016 for U.S. Appl. No. 14/198,757.
Office Action dated Sep. 10, 2015 for U.S. Appl. No. 14/198,757.
Office Action dated Dec. 27, 2017 for U.S. Appl. No. 14/864,361.
Office Action dated Nov. 7, 2019 for U.S. Appl. No. 14/864,361.
European Search Report dated Mar. 2, 2020 for EP15844212.9.
Office Action dated Jan. 20, 2023 for U.S. Appl. No. 17/146,981.

* cited by examiner

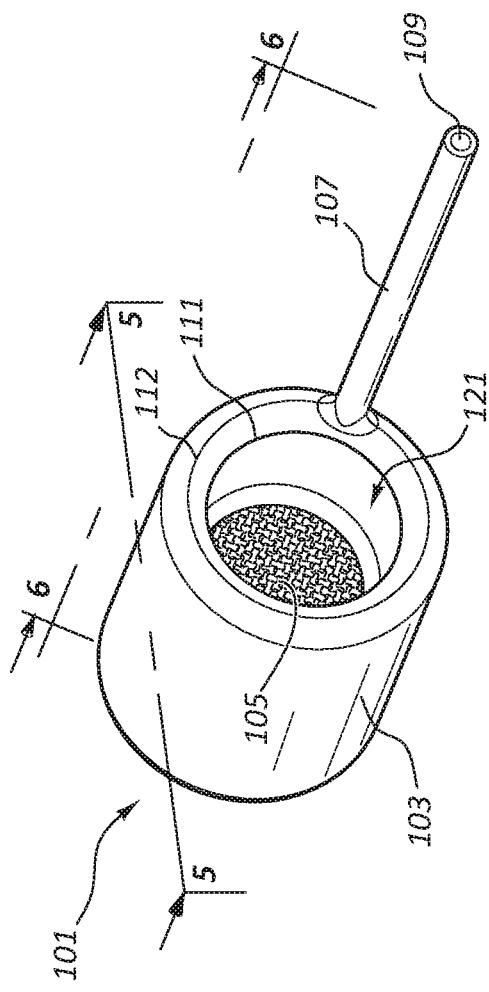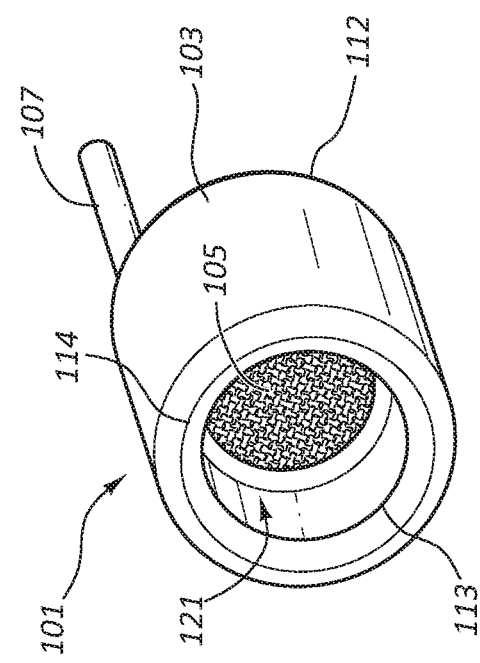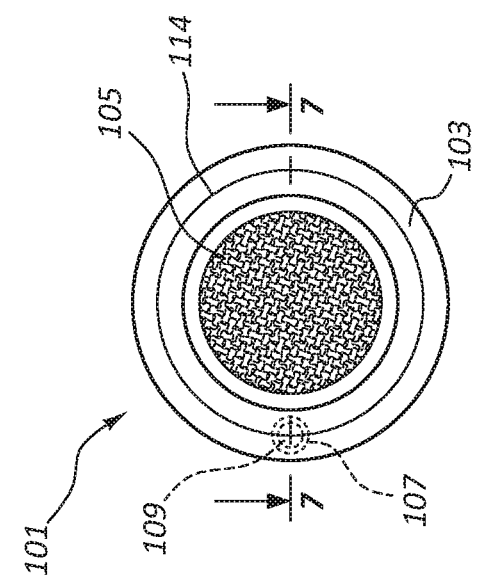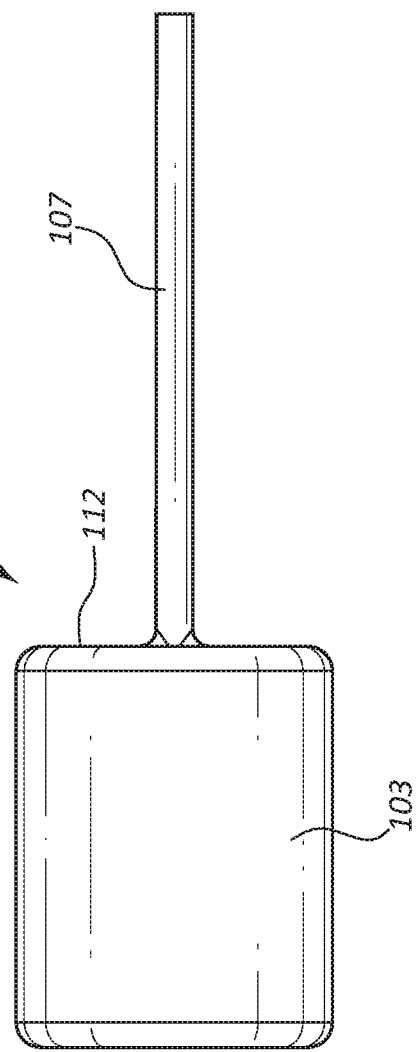

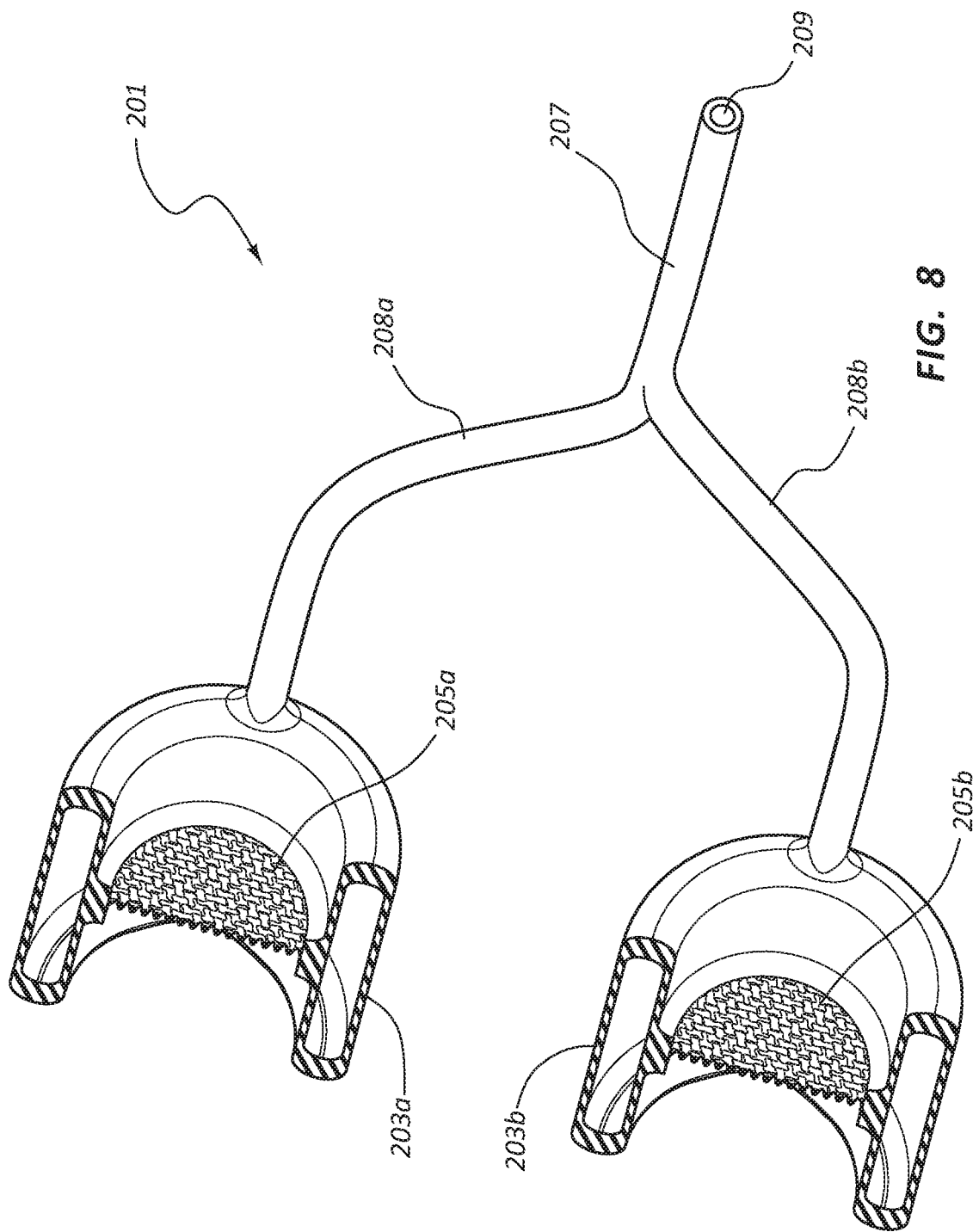

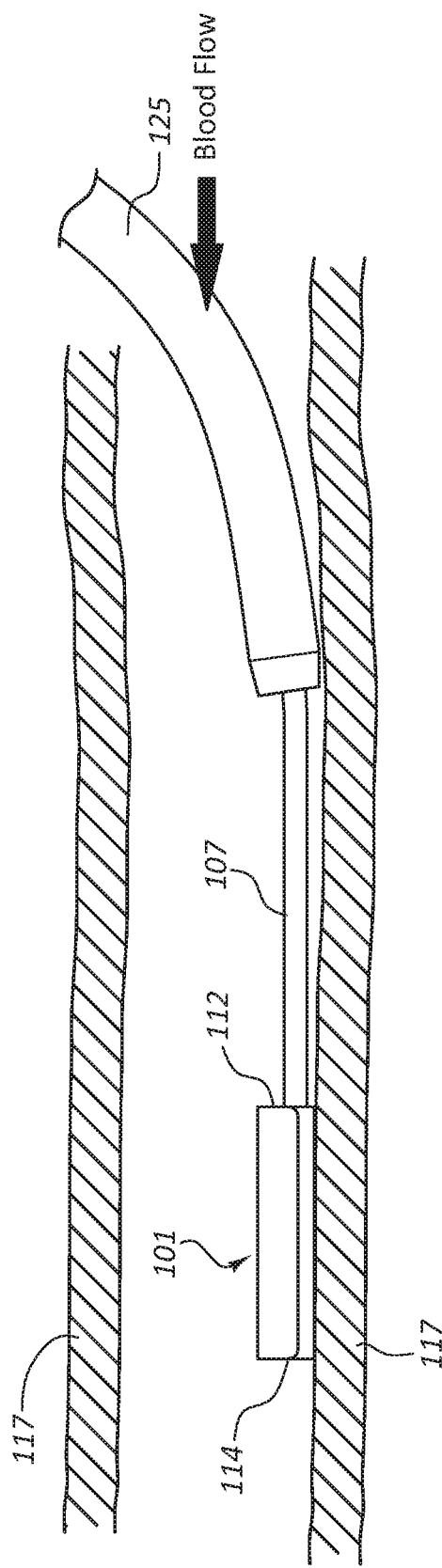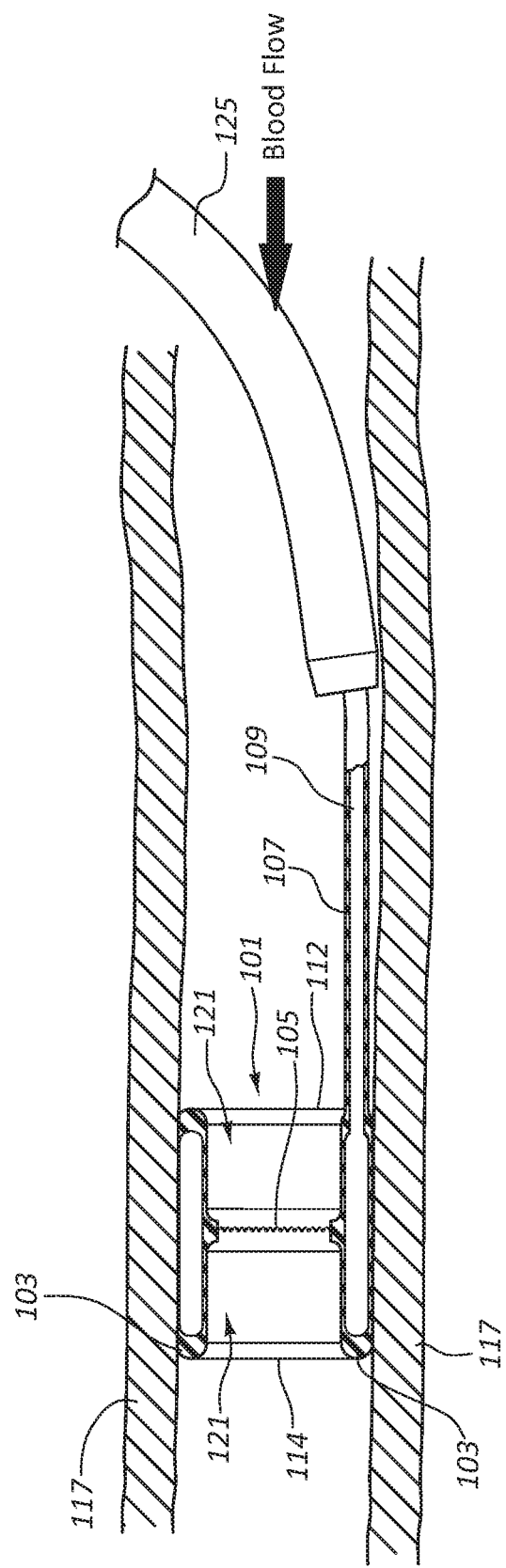

METHODS OF MANUFACTURING AN EMBOLIC FILTER BALLOON

RELATED APPLICATION

This application is a continuation of U.S. patent application Ser. No. 14/198,757, now abandoned, filed Mar. 6, 2014, titled "EMBOLIC FILTER BALLOON," which claims priority to U.S. Provisional Application No. 61/773,999 filed on Mar. 7, 2013, titled "EMBOLIC FILTER BALLOON," the entire contents of each of which are hereby incorporated by reference.

TECHNICAL FIELD

The present disclosure relates generally to medical devices. More specifically, the present disclosure relates to medical appliances such as embolic filters and related components for use in capturing or filtering particles, emboli, fragments, thrombi, or other debris from a fluid in a body lumen. In some embodiments, an embolic filter may comprise an inflatable balloon portion, including embodiments wherein the inflatable balloon portion is coupled to a filter member. An embolic filter balloon may be retrievably deployed in a body lumen, and the filter member may capture or filter particles, emboli, fragments, thrombi, or other debris from a fluid in the body lumen.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1 is a perspective view of a first embodiment of an embolic filter balloon showing the distal end thereof.

FIG. 2 is a perspective view of the embolic filter balloon of FIG. 1 showing the proximal end thereof.

FIG. 3 is a top view of the embolic filter balloon of FIG. 1.

FIG. 4 is a distal end view of the embolic filter balloon of FIG. 1.

FIG. 8 is a cross-sectional perspective view of an embolic filter balloon system having two inflatable balloon portions.

FIG. 16A is a side view of an embolic filter balloon, disposed in a vessel in a delivery configuration.

FIG. 16B is a side cross-sectional view of the embolic filter balloon of FIG. 16A, disposed in a vessel in an inflated configuration.

DETAILED DESCRIPTION

Figure 6:
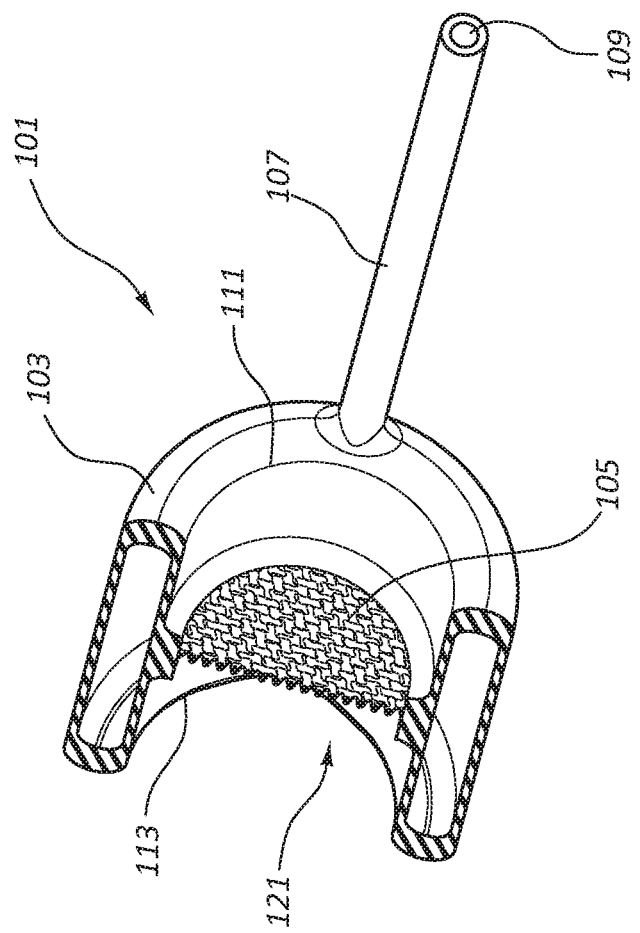
FIG. 6 is a cross-sectional perspective view of the embolic filter balloon of FIG. 2 taken through lines 6-6.

The term "particle" or its variants are used broadly throughout this disclosure to refer to any variety of emboli, fragments, thrombi, or other debris that may be released or dislodged into a fluid in a body lumen. Particles within the scope of this disclosure may comprise biologic and/or synthetic material and may or may not be introduced into the body by a medical practitioner. Some medical procedures or therapies may include the release of particles, including particles of body tissue or other biologic matter, into a fluid in a body lumen. For example, during expansion of a stent in a body lumen, particles may be dislodged into a fluid in the body lumen. In another example, deployment of a balloon catheter in a blood vessel during an angioplasty may result in particles of plaque and/or other debris being dislodged into the bloodstream. In yet another example, introduction of emboli (i.e., microspheres) into a target vessel to occlude blood flow to a tumor or other undesirable growth or lesion may result in at least a portion of the emboli being introduced into a non-target vessel.

Particles, emboli, fragments, thrombi, or other debris released into a fluid of a body lumen may result in ischemia, myocardial infarction, stroke, and other potentially adverse medical conditions. Some medical appliances may be configured for capturing or filtering such particles from a fluid in a body lumen. In some instances, medical appliances may be configured to filter or capture particles larger than a predetermined size from a fluid in a body lumen. For example, filters, meshes, or other porous members may be used to capture such particles from a fluid in a body lumen. Embolic filters may be introduced into a body lumen to capture particles from a fluid in the body lumen. In some embodiments, embolic filters may comprise inflatable balloon portions, including configurations wherein the inflatable balloon portion is coupled to a filter member. Such embolic filter balloons may be configured to capture or filter particles from a fluid in a body lumen.

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The term "balloon" is used broadly throughout this disclosure to refer to a variety of inflatable components of medical appliances having a variety of shapes, characteristics, and uses. Further, disclosure of concepts provided in connection with embodiments or examples reciting particular shapes, structures, or uses may be analogously applied to any inflatable components of medical appliances.

Also, the phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

Additionally, the terms "proximal" and "distal" refer to opposite ends of a medical appliance. As used herein, the proximal end of a medical appliance is the end nearest a practitioner during use, while the distal end is the opposite end. For example, the proximal end of an embolic filter balloon refers to the end nearest the practitioner when the embolic filter balloon is disposed within, or being deployed from, a deployment device. For consistency throughout, these terms remain constant in the case of a deployed embolic filter balloon, regardless of the orientation of the embolic filter balloon within the body. In the case of an embolic filter balloon deployed through the radial artery of a patient, for example, the proximal end will be nearer the wrist of the patient and the distal end will be nearer the heart of the patient when the embolic filter balloon is in a deployed position.

An inflatable balloon portion of an embolic filter balloon may comprise a wall defining the interior portion of the inflatable balloon portion and separating the interior portion from the external environment. As the inflatable balloon portion is inflated, inflation fluid may be introduced into the interior portion, exerting pressure on the wall of the inflatable balloon portion. In some procedures, the wall may be used to conform the inflatable balloon portion to the interior diameter of a body lumen. Further, in some instances, an additional catheter or other medical appliance may also be disposed within the body lumen adjacent to the embolic filter balloon, in these instances the wall may be used to conform the inflatable balloon portion to both the interior diameter of the body lumen and the exterior surface of the additional catheter or other medical appliance. Thus, an embolic filter balloon may generally restrict fluid flow through a body lumen while allowing a catheter or other instrument to bypass the filter.

In some embodiments the inflatable balloon portion may be configured with a "flow through" type design, which may allow blood or other fluids to pass through the inflatable balloon portion while the inflatable balloon portion is in an inflated state. For example, an inflatable balloon portion may be shaped like a hollow cylinder, allowing the inflatable balloon portion to be inflated within a vessel, while still allowing blood to pass through the center of the inflatable balloon portion. In another embodiment, an embolic filter balloon may be comprised of an inflatable balloon portion configured with an interior fluid flow path, wherein a filter member may be coupled to the interior fluid flow path, which may allow the embolic filter balloon to filter or capture particles larger than a predetermined size from the fluid flowing through the interior fluid flow path. An embolic filter balloon comprising an interior fluid flow path may direct at least a portion of a fluid flowing through a body lumen through the interior fluid flow path. For example, an embolic filter balloon may be inflated within a body lumen at a position downstream from a site of a vascular procedure, during the vascular procedure particles may be dislodged into the bloodstream, and the embolic filter balloon may filter or capture the dislodged particles from the bloodstream.

FIG. 1 is a perspective view of a first embodiment of an embolic filter balloon 101 showing a distal end 114 thereof. As shown in FIG. 1, an embolic filter balloon 101 comprises an inflatable balloon portion 103, a filter member 105, and a catheter portion 107. In the illustrated embodiment, the filter member 105 is coupled to the inflatable balloon portion 103, and the catheter portion 107 is in fluid communication with the inflatable balloon portion 103. Other configurations of these and other components of an embolic filter balloon are also within the scope of this disclosure.

In some embodiments, the inflatable balloon portion 103 of the embolic filter balloon 101 may be configured to at least partially conform to an interior diameter of a body lumen when the inflatable balloon portion 103 is deployed or inflated. For example, the inflatable balloon portion 103 may be tube-shaped, cylindrical, or otherwise shaped. Any size of inflatable balloon portion 103 of any geometry is also within the scope of this disclosure. The shape of the inflatable balloon portion 103 may be selected or designed to conform to the shape of an interior diameter of a target body lumen. As used herein, a target body lumen may be any body lumen, or any position within a body lumen, wherein a practitioner or user may desire to deploy a medical appliance such as an embolic filter balloon 101.

One or more additional catheters or other instruments may also pass through the target body lumen or be disposed at or adjacent to the target body lumen. In some embodiments, the inflatable balloon portion 103 may be configured to conform to both the interior diameter of the target body lumen and the exterior surface of the one or more catheters or other instruments that may pass through or be disposed at or adjacent to the target body lumen. Further, the inflatable balloon portion 103, when at least partially inflated, may be configured to substantially form a seal between the exterior surface of the inflatable balloon portion 103 and both the interior diameter of the target body lumen and the exterior surface or surfaces of the one or more catheters or other instruments that may pass through or be positioned at or adjacent to the target body lumen.

In the illustrated embodiment, the inflatable balloon portion 103 comprises an interior fluid flow path 121. The interior fluid flow path 121, comprising a distal opening 113 and a proximal opening 111 as shown in FIG. 2, may allow a fluid or other material to flow through an inflatable balloon portion 103 even though the inflatable balloon portion 103 is in an inflated state. For example, an inflatable balloon portion 103 comprising an interior fluid flow path 121 may conform to an inside diameter of a vessel when deployed, but may still permit flow of blood through the interior fluid flow path 121. Such a configuration may permit a substantially continuous flow of blood through the vessel. In some instances, it may not be desirable to substantially decrease or fully occlude flow of fluid through a body lumen. For example, adverse medical conditions may result due to a flow decrease or occlusion of blood flow through a vessel.

As illustrated in FIG. 1, the filter member 105 may be positioned in the interior fluid flow path 121 at a position between a proximal end 112 and a distal end 114 of the inflatable balloon portion 103. In another embodiment, the filter member 105 may be coupled to the inflatable balloon portion 103 such that the filter member 105 is configured to allow passage only of particles of less than a predetermined size through a body lumen when the inflatable balloon portion 103 is deployed or inflated.

Use of embolic filters comprising one or more inflatable balloon portions, like the inflatable balloon portion 103, may facilitate various aspects of procedures and/or therapies involving embolic filters. For example, an embolic filter comprising one or more inflatable balloon portions may possess enhanced flexibility in comparison to embolic filters comprising wires, baskets, netting, or analogous components. The inflatable balloon portion may enable an embolic filter balloon, like the embolic filter balloon 101, to be folded or otherwise packed into a smaller delivery configuration. Embolic filters with smaller delivery profiles may be introduced at more locations in a mammalian body than larger embolic filters, which may facilitate treatment and access. Additionally, smaller profiles may require smaller access openings, which may decrease bleeding, trauma, and complications.

Also, as further detailed below, an embolic filter comprising one or more inflatable balloon portions may filter or capture a greater proportion of particles from a fluid in a body lumen than filtered or captured by an embolic filter comprising wires, baskets, netting, or other analogous components. For example, an embolic filter comprising one or more inflatable balloon portions may form a better seal between an exterior surface or surfaces of the one or more inflatable balloon portions and an interior diameter of a body lumen than may be formed by analogous components of an embolic filter comprising wires, baskets, netting, or other analogous components. More specifically, when deployed, the embolic filter comprising one or more inflatable balloon portions may form substantially more points of contact with the interior diameter of the body lumen than formed by the embolic filter comprising wires, baskets, netting, or other analogous components. Such an enhanced seal may provide enhanced filtration or capture of particles from the fluid of the target body lumen. Additionally, embolic filters comprising one or more inflatable balloon portions may also pass more easily through body lumens, cause less trauma to vessel walls, and be more easily retrieved from body lumens than embolic filters comprising wires, baskets, netting, or other analogous components. For example, an embolic filter comprising one or more inflatable balloon portions may be softer, more pliable, and/or less abrasive than an embolic filter comprising wires, baskets, netting, or other analogous components.

FIG. 2 is a perspective view of the embolic filter balloon 101 of FIG. 1 showing the proximal end 112 thereof. As shown, the position of the filter member 105 coupled to the interior fluid flow path 121 may be viewed from the proximal end 112 of the embolic filter balloon 101. In some embodiments, the catheter portion 107 may be coupled to the inflatable balloon portion 103 at the proximal end 112 of the inflatable balloon portion 103, and/or the catheter portion 107 may be coupled to the inflatable balloon portion 103 at a position adjacent to the proximal opening 111 of the inflatable balloon portion 103. The catheter portion 107 may be coupled to the inflatable balloon portion 103 at any location on, or adjacent to, the inflatable balloon portion 103. Further, any positioning or variety of coupling between the catheter portion 107 and the inflatable balloon portion 103 is within the scope of this disclosure.

As illustrated in FIG. 2, the catheter portion 107 may comprise an inflation lumen 109. In some embodiments, the inflation lumen 109 may be configured to deliver an inflation fluid from an inflation device to the inflatable balloon portion 103 to at least partially inflate the inflatable balloon portion 103. In yet another embodiment, the inflation lumen 109 may be configured to remove or evacuate an inflation fluid from the inflatable balloon portion 103 to at least partially deflate the inflatable balloon portion 103. For example, an inflation fluid may be removed from the inflatable balloon device via the inflation lumen 109 to an inflation device.

FIG. 3 is a top view of the embolic filter balloon 101 of FIG. 1. The embodiment illustrated in FIG. 3 shows one possible coupling between the inflatable balloon portion 103 and the catheter portion 107, wherein the catheter portion 107 may be coupled to the inflatable balloon portion 103 adjacent to the proximal end 112 of the inflatable balloon portion 103.

Figure 5:
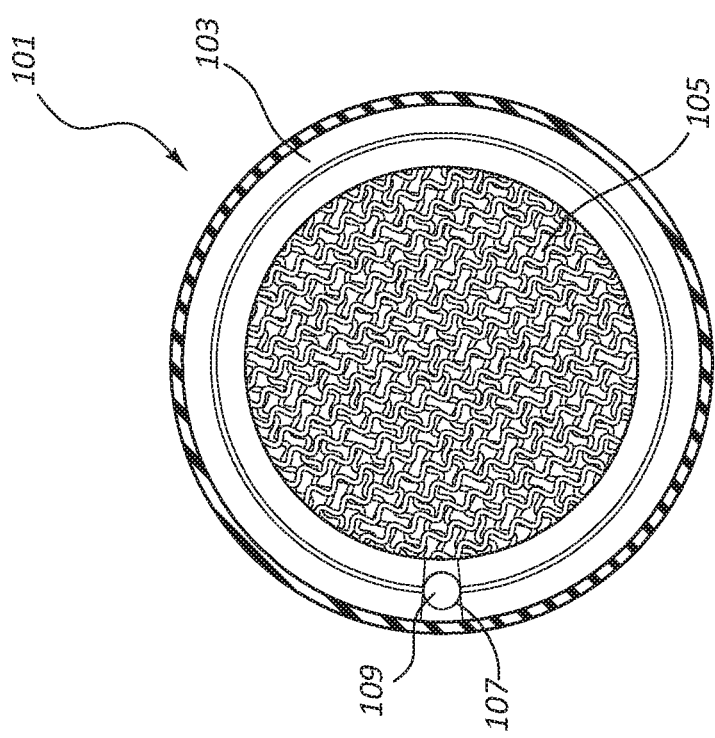
FIG. 5 is a cross-sectional view of the embolic filter balloon of FIG. 2 taken through lines 5-5.

FIG. 4 is a distal end 114 view of the embolic filter balloon 101 of FIG. 1, and FIG. 5 is a cross-sectional view of the embolic filter balloon 101 of FIG. 2 taken through lines 5-5. As shown in the illustrated embodiment, the inflatable balloon portion 103 may be substantially cylindrical, comprising the distal end 114. One configuration of the catheter portion 107 comprising the inflation lumen 109 is also illustrated. Additionally, the embolic filter balloon 101 may further comprise the filter member 105 coupled to the inflatable balloon portion 103 at a position within or adjacent to an interior diameter of the inflatable balloon portion 103. When at least partially inflated, the inflatable balloon portion 103 may substantially conform to the interior diameter of a body lumen. Such a configuration may direct or result in at least a portion of a fluid flowing through a body lumen to flow or pass through the inflatable balloon portion 103 and the filter member 105. In some instances, substantially all particles greater than a predetermined size may be captured or filtered from a fluid in a body lumen when the fluid flows or passes through the inflatable balloon portion 103 and the filter member 105.

The filter member 105 may allow a fluid to flow through a body lumen while controlling or limiting the flow of particles through the body lumen. For example, the filter member 105 may be configured to filter or capture particles larger than a predetermined size from blood flowing through a vessel but allow the blood to pass through the filter member 105.

Embolic filter balloons 101 and components of embolic filter balloons 101 may be formed of a variety of materials, including, for example, elastic materials, elastomers, polymers, flexible materials, and so forth. Specifically, in some embodiments embolic filter balloons and the various components of embolic filter balloons may be formed of PEBAX, polytetrafluoroethylene (PTFE), nylon, silicone, or any thermoplastic material. A practitioner using an embolic filter balloon 101 comprising an elastic material, for example, may modify an inflation pressure of the embolic filter balloon 101 to optimize the seal between the exterior surface of the embolic filter balloon 101 and the interior diameter of a body lumen. In some instances, the interior diameter of the body lumen may comprise a challenging anatomy, defined as a body lumen wherein, for example: the interior diameter of the body lumen is not uniform; the body lumen is curved or abnormally shaped; the body lumen is altered by an injury, medical condition, or medical treatment; and so forth. In such situations, the embolic filter balloon 101 comprising the elastic material may provide enhanced conformance between the outside surface of the embolic filter balloon 101 and the interior diameter of the body lumen comprising the challenging anatomy, as compared to embolic filter balloons comprising non-elastic materials.

In some other embodiments, at least one of the inflatable balloon portion 103 and the filter member 105 may comprise electrospun nano-fibers or micro-fibers, or rotationally spun nano-fibers or micro-fibers. Specifically, the electrospun nano-fibers or micro-fibers, or the rotationally spun nano-fibers or micro-fibers may be comprised of at least one of the following: polyamide, aromatic polyimide, polyethylene, and polypropylene. Processes for electrospinning nano-fibers or micro-fibers are described in U.S. Provisional Application No. 61/703,037, filed on Sep. 19, 2012, and titled "Electrospun Material Covered Medical Appliances and Methods of Manufacture"; and U.S. application Ser. No. 13/360,444, filed on Jan. 27, 2012, and titled "Electrospun PTFE Coated Stent and Method of Use." Both of these two applications are hereby incorporated by reference in their entirety. Likewise, processes for rotationally spinning nano-fibers or micro-fibers are described in U.S. application Ser. No. 13/742,025, filed on Jan. 15, 2013, and titled "Rotational Spun Material Covered Medical Appliances and Methods of Manufacture," which is hereby incorporated by reference in its entirety.

In one embodiment, the filter member 105 may be formed of a mat of electrospun nano-fibers or micro-fibers. In another embodiment, the filter member 105 may be formed of a mat of rotationally spun nano-fibers or micro-fibers. The porosity of the electrospun nano-fiber or micro-fiber mat may be modified as desired to create a filter that captures particles at a predetermined size. For example, a more porous mat will allow larger particles to pass, while a less porous mat can limit the size of particles to pass the filter.

Electrospun coatings and rotational spun coatings may be applied to any balloon substrate and may be configured to provide additional strength to the balloon, increase the puncture resistance of the balloon, provide a lubricious coating, and so forth. Electrospinning and rotational spinning may be used to coat a balloon with a matrix of fibers, including nano-fibers and/or micro-fibers. In some embodiments, the fibers may be on the nano-scale, meaning smaller than one micron in diameter. In other embodiments, the fibers may be on the micro-scale, meaning smaller than one millimeter in diameter.

In one embodiment, at least one of the inflatable balloon portion 103 and the filter member 105 may comprise a single layer. In another embodiment, at least one of the inflatable balloon portion 103 and the filter member 105 may comprise a plurality of layers. Multilayered balloon constructs and/or filter constructs may further increase the strength and usability of balloons and/or filters by decreasing the risk that manufacturing or material defects within the balloon and/or filter will compromise the integrity of the balloon and/or filter. In other words, a single layer balloon having a defect in the wall of the balloon will likely have a weak point at the defect. However, it is unlikely that a defect in one layer of a multilayered design will be aligned with a defect in an adjacent layer. Thus, the effect of any single defect may be minimized, as the defect area will be reinforced by portions of adjacent layers which are likely defect-free.

Similarly, the outside layer of a multilayer balloon may contact bodily structures or other medical appliances during delivery and/or use. Such contact may stretch, scratch, pierce, or otherwise weaken the layer. As with material defects, however, these points may be reinforced by adjacent layers which are not compromised. Conversely, such points on a single-layer design may more significantly affect the overall strength of the balloon. Thus, as opposed to a single-layer design, a multilayered design may be more robust, particularly for use in potentially damaging conditions.

FIG. 6 is a cross-sectional perspective view of the embolic filter balloon 101 of FIG. 2 taken through lines 6-6. In the illustrated embodiment, the filter member 105 may be positioned in the interior fluid flow path 121 of the inflatable balloon portion 103 at a position between the proximal opening 111 and the distal opening 113 of the inflatable balloon portion 103. The inflatable balloon portion 103 and the filter member 105 may be formed of the same material. Alternatively, the inflatable balloon portion 103 may be formed of a different material than the filter member 105. Additionally, the catheter portion 107, comprising the inflation lumen 109, may be formed of the same material as the inflatable balloon portion 103 and/or the filter member 105. Alternatively, the catheter portion 107 may be formed of a different material than the inflatable balloon portion 103 and/or the filter member 105. The filter member 105 may be formed of any porous material. For example, the filter member 105 may comprise a porous material, such as a mesh, a woven material, and so forth. Specifically, the filter member 105 may comprise a material that may be formed by expansion, extrusion, melt blowing, molding, sewing, weaving, and other comparable techniques. The filter member 105 may be coupled to the inflatable balloon portion 103, for example, by adhesive, bonding, heat bonding, stitching, and other analogous methods.

In some embodiments, the filter member 105 may be coated, loaded or associated with a therapeutic agent, such as a drug. The therapeutic agent may be configured to be released into a fluid in a body lumen, or into tissue adjacent a body lumen. For example, the filter member 105 may be positioned in a vessel, and as blood flows through the filter member 105, the therapeutic agent may be controllably released into the blood. Such a configuration may provide an interoperative method for enhanced delivery of a therapeutic agent into the bloodstream of a patient. In embodiments where the filter member 105 comprises electrospun or rotationally spun nano-fibers or micro-fibers, the filter member 105 may comprise an increased surface area as compared to embodiments where the filter member 105 does not comprise electrospun or rotationally spun nano-fibers or micro-fibers. Such an increased surface area, when coated with or coupled to a therapeutic agent, may provide for enhanced or controlled delivery of the therapeutic agent into the bloodstream.

In a more specific embodiment, the filter member 105 may be coated with or coupled to an anti-thrombotic agent. In one embodiment, the anti-thrombotic agent is covalently or ionically bound to the filter member 105. The anti-thrombotic agent may be configured to reduce or prevent thrombus formation on the filter member 105. Anti-thrombotic agents, when coating or coupled to the filter member 105, may allow the filter member 105 to capture or filter particles larger than a predetermined size from a fluid in a body lumen while also reducing thrombus formation on the filter member 105. Additionally, reduction in thrombus formation may reduce shear on the fluid flowing through the filter member 105. For example, a practitioner may position an embolic filter balloon 101 in a vessel, where the filter member 105 is coated with or otherwise associated with an anti-thrombotic agent. The anti-thrombotic agent may reduce or prevent thrombus formation on or adjacent to the filter member 105, and such reduction and/or prevention of thrombus formation on or adjacent to the filter member 105 may allow substantially continuous flow of blood through the filter member 105.

Figure 7:
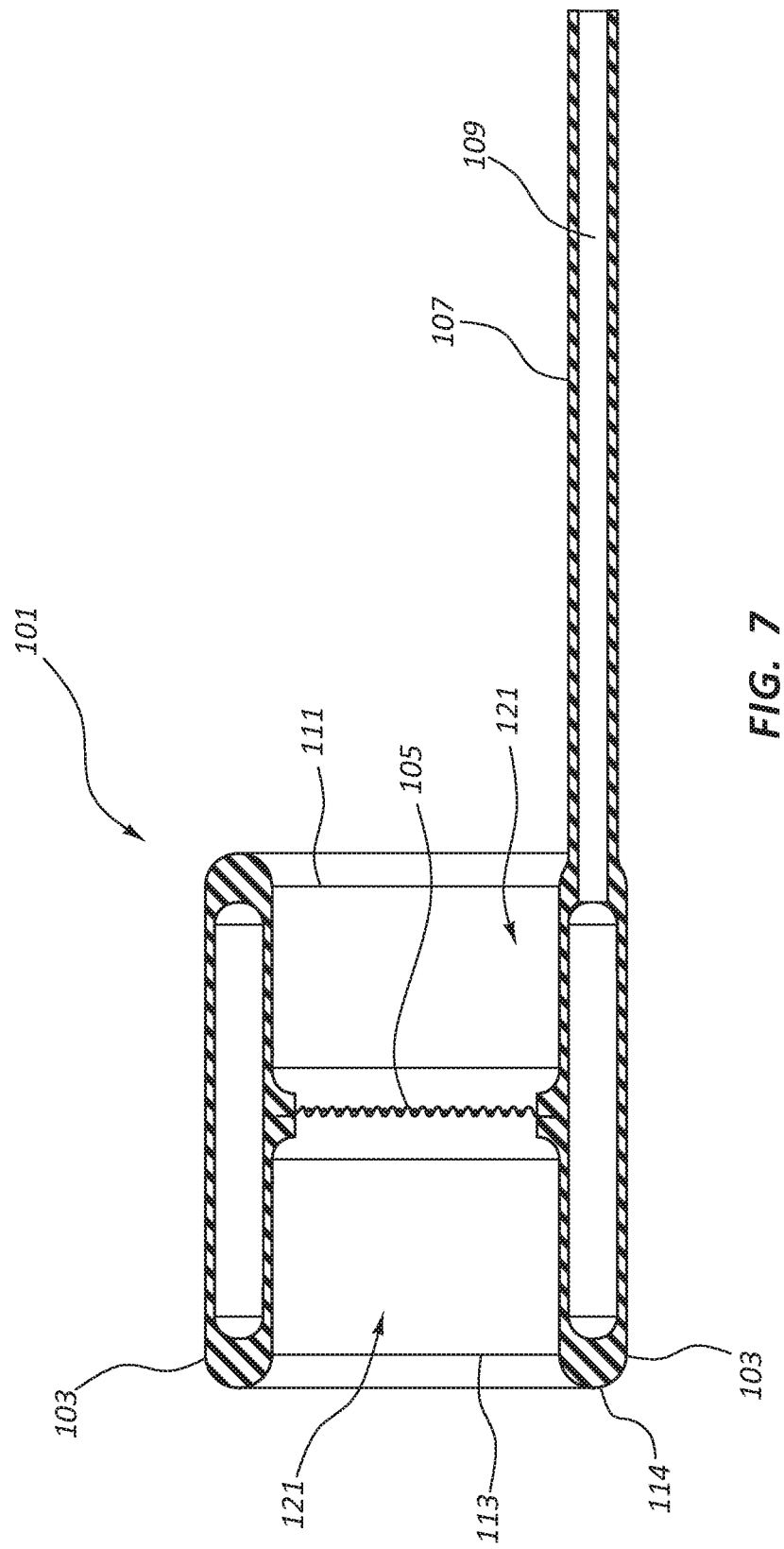
FIG. 7 is a cross-sectional view of the embolic filter balloon of FIG. 4 taken through lines 7-7.

FIG. 7 is a cross-sectional view of the embolic filter balloon 101 of FIG. 4 taken through lines 7-7. As illustrated, the filter member 105 extends across the internal fluid flow path 121 at a position between the proximal 111 and the distal 113 openings of the inflatable balloon portion 103. Further, as illustrated, the catheter portion 107 may comprise the inflation lumen 109 in fluid communication with the inflatable balloon portion 103. As described above, the inflation lumen 109 may be configured to deliver an inflation fluid from an inflation device to the inflatable balloon portion 103 to at least partially inflate the inflatable balloon portion 103. The inflation lumen 109 may also be configured to remove an inflation fluid from the inflatable balloon portion 103 to at least partially deflate the inflatable balloon portion 103. In embodiments, the degree of inflation or deflation of the inflatable balloon portion 103 may be controlled by increasing or decreasing the amount of an inflation fluid flowing into or out of the inflatable balloon portion 103. In other embodiments, the rate of inflation or deflation of the inflatable balloon portion 103 may be controlled by increasing or decreasing the flow rate of an inflation fluid into or out of the inflatable balloon portion 103.

In another embodiment, an inflation lumen, like the inflation lumen 109, may extend through an inflatable balloon portion, like the inflatable balloon portion 103, and may be in at least partial fluid communication with a distal end, like the distal end 114, of the inflatable balloon portion. A catheter portion, like the catheter portion 107, may also comprise a plurality of catheter lumens. For example, the catheter portion may comprise a double-D lumen catheter. In embodiments, the catheter portion may comprise a first lumen comprising an inflation lumen in fluid communication with the inflatable balloon portion. The catheter portion may also extend through the inflatable balloon portion and further comprise a second lumen comprising, for example, a delivery lumen configured to provide a sleeve or sheath for delivery of a medical appliance to a position in a body lumen distal to the inflatable balloon portion. In another example, the first catheter lumen may comprise an inflation lumen in fluid communication with the inflatable balloon portion, and the second catheter lumen may comprise, for example, a delivery lumen configured to provide a sleeve or sheath for delivery of a medical appliance to a position proximal to the embolic filter balloon.

In yet another example, the catheter portion may comprise more than two lumens wherein a first lumen is in fluid communication with the inflatable balloon portion, a second lumen comprises a delivery lumen configured to provide a sleeve or sheath for delivery of a medical appliance or appliances to a position distal to and/or proximal to the embolic filter balloon, a third lumen comprises a delivery lumen configured to provide a sleeve or sheath for delivery of a medical appliance or appliances to a position distal to and/or proximal to the embolic filter balloon, and so forth. In some embodiments, the lumens may comprise inflation lumens, delivery lumens, or other varieties of lumens. For example, a lumen or lumens of the catheter portion may be configured to provide at least one of the following: a sleeve or sheath for delivery of a medical device, a passageway for delivery of a therapeutic agent, and a passageway for delivery of an inflation fluid to one or more balloon catheters.

In some embodiments, the catheter portion may comprise a lumen configured to deliver medications, embolic microspheres, or other therapies to a position in a body lumen either upstream or downstream of a filter member, like filter member 105. For example, a practitioner may desire to deliver embolic microspheres to a target vessel in order to intentionally occlude blood flow to a fibroid, tumor, cancer, or other undesirable growth or lesion. To prevent the embolic microspheres from migrating to and at least partially occluding a non-target vessel, the practitioner may deliver the embolic microspheres via the catheter portion to a position upstream from the filter member, wherein the filter member may capture or filter misdelivered embolic microspheres. In additional embodiments, the number of lumens may correspond to the number of medical appliances coupled to or delivered through the catheter portion. Medical appliances in these and other embodiments herein disclosed comprise, but are not limited to: balloons, catheters, embolic delivery devices, filters, guide wires, introducers, retrieval devices, snares, and stents.

In another embodiment, a filter member, like the filter member 105, may be coupled to an inflatable balloon portion, like the inflatable balloon portion 103, at or adjacent to at least one of a distal end or a proximal end of the inflatable balloon portion. Further, the inflatable balloon portion may be configured to perform a balloon angioplasty procedure. For example, a practitioner may use such an embodiment to perform a balloon angioplasty procedure, wherein the filter member may capture or filter particles or emboli greater than a predetermined size that may be released during the balloon angioplasty procedure. Specifically, such an embodiment may be used by a practitioner for a carotid percutaneous transluminal angioplasty (PTA).

FIG. 8 is a cross-sectional perspective view of an embolic filter balloon system 201 having a first inflatable balloon portion 203a and a second inflatable balloon portion 203b. The embodiment of FIG. 8 may include components that resemble components of the embodiment of FIGS. 1-7 in some respects. For example, the embodiment of FIG. 8 includes the first inflatable balloon portion 203a that may resemble the inflatable balloon portion 103 of FIGS. 1-7. It will be appreciated that all the illustrated embodiments have analogous features. Accordingly, like features are designed with like reference numerals, with leading digits added to increment each reference numeral by 100. (For instance, the inflatable balloon portion is designated "103" in FIG. 1 and analogous inflatable balloon portions are designated as "203a" and "203b" in FIG. 8.) Relevant disclosure set forth above regarding similarly identified features thus may not be repeated hereafter. Moreover, specific features of the embolic filter balloon system and related components shown in FIG. 8 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the embolic filter balloon system and related components of FIG. 8. Any suitable combination of the features, and variations of the same, described with respect to the embolic filter balloon and components illustrated in FIGS. 1-7, can be employed with the embolic filter balloon system and components of FIG. 8, and vice versa. This pattern of disclosure applies equally to further embodiments depicted in subsequent figures and/or described hereafter.

In the embodiment of FIG. 8, an embolic filter balloon system 201 may comprise a bifurcated catheter portion 207 comprising a first arm 208a and a second arm 208b. The embolic filter balloon system 201 may further comprise the first inflatable balloon portion 203a coupled to the first arm 208a and the second inflatable balloon portion 203b coupled to the second arm 208b. The first 203a and second 203b inflatable balloon portions may both be configured to at least partially conform to an inside diameter of a single body lumen when the first 203a and second 203b inflatable balloon portions are deployed or inflated. In another embodiment, the first 203a and second 203b inflatable balloon portions may be configured to at least partially conform to two inside diameters of two separate body lumens respectively when the first 203a and second 203b inflatable balloon portions are deployed or inflated.

Additionally, the first inflatable balloon portion 203a may be coupled to a first filter member 205a, and the second inflatable balloon portion 203b may be coupled to a second filter member 205b. The first 205a and second 205b filter members may be configured to allow passage only of particles less than a predetermined size in the fluid of the one or more body lumens when the first 203a and second 203b inflatable balloon portions are deployed or inflated. The bifurcated catheter portion 207 may further comprise a bifurcated inflation lumen 209, wherein the bifurcated catheter portion 207 may be in fluid communication with the first inflatable balloon portion 203a and the second inflatable balloon portion 203b, and may further be configured to at least partially inflate or deploy the first inflatable balloon portion 203a and the second inflatable balloon portion 203b. In such an embodiment, the first 203a and the second 203b inflatable balloon portions may be inflated or deflated substantially together.

In another embodiment, a bifurcated catheter portion, like the bifurcated catheter portion 207, may comprise a plurality of lumens and/or bifurcated lumens. For example, a first inflatable balloon portion, like the inflatable balloon portion 203a, may be in fluid communication with a first inflation lumen, and a second inflatable balloon portion, like the second inflatable balloon portion 203b, may be in fluid communication with a second inflation lumen. In such a configuration, the first inflatable balloon portion and the second inflatable balloon portion may be inflated or deflated substantially independent of one another. For example, a practitioner may inflate a first inflatable balloon portion while maintaining a second inflatable balloon portion in a pre-inflated state, or vice versa.

In an embodiment, the embolic filter balloon system 201 may be deployed in two separate lumens of a branched body lumen. For example, a single vessel may branch into two or more vessels in a region downstream of a site of a vascular procedure or therapy. The embolic filter balloon system 201 may be deployed to capture or filter particles from a fluid flowing through such branched vessels.

In other embodiments, an embolic filter balloon system, like the embolic filter balloon system 201, may comprise more than two inflatable balloon portions. For example, a body lumen may branch into three body lumens. In such a body lumen, an embolic filter balloon system comprising three inflatable balloon portions may be used. Embodiments with a plurality of inflatable balloon portions and a plurality of other embolic filter balloon components are also within the scope of this disclosure.

Figure 9:
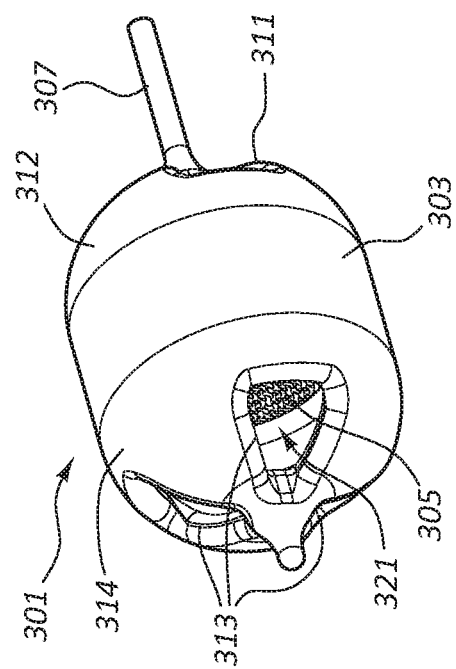
FIG. 9 is a perspective view of another embodiment of an embolic filter balloon showing the distal end thereof.

FIG. 9 is a perspective view of another embodiment of an embolic filter balloon 301 showing the distal end 314 thereof. The embolic filter balloon 301 of FIG. 9 may be comprised of an inflatable balloon portion 303, a filter member 305, and a catheter portion 307. In the illustrated embodiment, the filter member 305 is coupled to the inflatable balloon portion 303, and the catheter portion 307 is in fluid communication with the inflatable balloon portion 303. Other configurations of these and other components of an embolic filter balloon, however, are also within the scope of this disclosure.

In some embodiments, the inflatable balloon portion 303 of the embolic filter balloon 301 may be configured to at least partially conform to an interior diameter of a body lumen when the inflatable balloon portion 303 is deployed or inflated. In the embodiment of FIG. 9, the inflatable balloon portion 303 is cylindrical and comprises substantially rounded proximal 312 and distal 314 ends. Such a configuration may facilitate deployment and/or adjustment of the embolic filter balloon 301 within a body lumen. For example, the substantially rounded proximal 312 and distal 314 ends may decrease the potential for the embolic filter balloon 301 to damage or injure a body lumen or other body feature. As described above, the inflatable balloon portion 303 may also be tube-shaped, cylindrical, or otherwise shaped. The shape of the inflatable balloon portion 303 may be selected or designed to conform to the shape of an interior diameter of a target body lumen. Any size of inflatable balloon portion 303 of any geometry is also within the scope of this disclosure.

Figure 10:
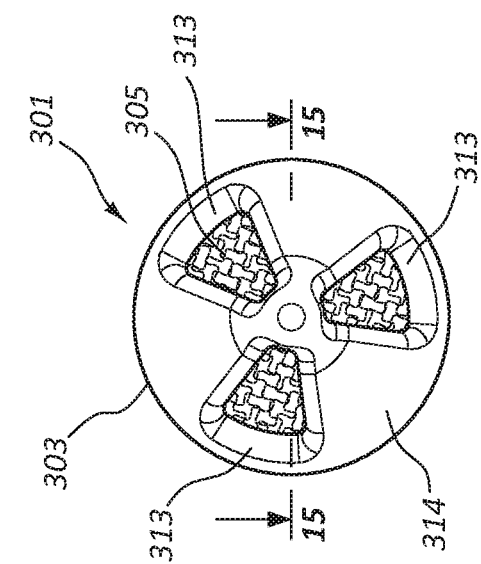
FIG. 10 is a perspective view of the embolic filter balloon of FIG. 9 showing the proximal end thereof.

In the illustrated embodiment, the inflatable balloon portion 303 comprises an interior fluid flow path 321. The interior fluid flow path 321 may allow a fluid to flow through the inflatable balloon portion 303 even though the inflatable balloon portion 303 is in an inflated state. In the embodiment as illustrated in FIGS. 9 and 10, the embolic filter balloon 301 comprises three proximal openings 311 at the proximal end 312 of the embolic filter balloon 301 and three distal openings 313 at the distal end 314 of the embolic filter balloon 301. The proximal openings 311 and the distal openings 313 may provide communication between the interior fluid flow path 321 and a fluid in or flowing through a body lumen at either or both the proximal 312 and distal 314 ends of the embolic filter balloon 301. In other embodiments there may be one, two, four, or more openings to the interior fluid flow path 321. As described above, the embolic filter balloon 301 may conform to an inside diameter of a blood vessel when deployed but may still permit flow of blood through the inflatable balloon portion 303. Such a configuration may permit an at least partial flow of blood through a vessel.

As illustrated in FIG. 9, the filter member 305 may be positioned in the interior fluid flow path 321 at a position between the proximal openings 311 and the distal openings 313 of the inflatable balloon portion 303. In another embodiment, the filter member 305 may be coupled to the inflatable balloon portion 303 such that the filter member 305 is configured to allow passage only of particles of less than a predetermined size through the body lumen when the inflatable balloon portion 303 is deployed or inflated.

FIG. 10 is a perspective view of the embolic filter balloon 301 of FIG. 9 showing the proximal end 312 thereof. As illustrated, the position of the filter member 305 within the interior diameter of the inflatable balloon portion 303 may be viewed through the proximal openings 311. In some embodiments, the catheter portion 307 may be coupled to the inflatable balloon portion 303 at the proximal end 312 of the inflatable balloon portion 303, or the catheter portion 307 may be coupled to the inflatable balloon portion 303 at a position adjacent to the proximal end 312 of the inflatable balloon portion 303. As described above, the catheter portion 307 may couple the inflatable balloon portion 303 at any location on, or adjacent to, the inflatable balloon portion 303, and any variety of coupling between the catheter portion 307 and the inflatable balloon portion 303 is within the scope of this disclosure.

The catheter portion 307 may comprise an inflation lumen 309. In some embodiments, the inflation lumen 309 may be configured to deliver an inflation fluid from an inflation device to the inflatable balloon portion 303 to at least partially inflate the inflatable balloon portion 303. In yet another embodiment, the inflation lumen 309 may be configured to remove or evacuate an inflation fluid from the inflatable balloon portion 303 to at least partially deflate the inflatable balloon portion 303. For example, an inflation fluid may be removed from the inflatable balloon portion 303 via the inflation lumen 309 to an inflation device.

Figure 11:
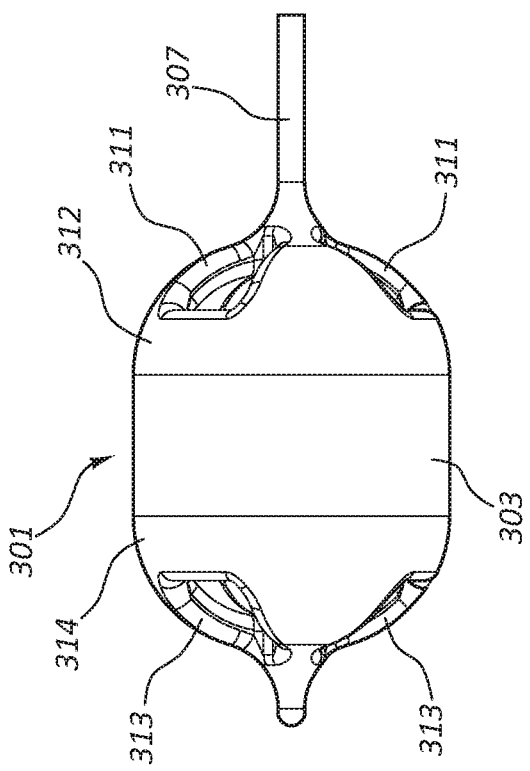
FIG. 11 is a top view of the embolic filter balloon of FIG. 9.

FIG. 11 is a top view of the embolic filter balloon 301 of FIG. 9. The catheter portion 307 may couple to the inflatable balloon portion 303 at the proximal end 312 of the inflatable balloon portion 303. Additionally, proximal openings 311 and distal openings 313 are positioned adjacent to the proximal end 312 and the distal end 314, respectively, of the embolic filter balloon 301. In the embodiment of FIG. 11, the catheter portion 307 is coupled to the inflatable balloon portion 303 at a position parallel to and adjacent to a central axis of the inflatable balloon portion 303. Such a configuration may, at least partially, prevent the catheter portion 307 from contacting the interior diameter of the body lumen at or near the site of deployment of the embolic filter balloon 301, and may decrease the potential for injury to an interior surface of the body lumen. Such a configuration may also enhance fluid flow in a region of the body lumen adjacent to the deployment of the embolic filter balloon 301.

Figure 12:
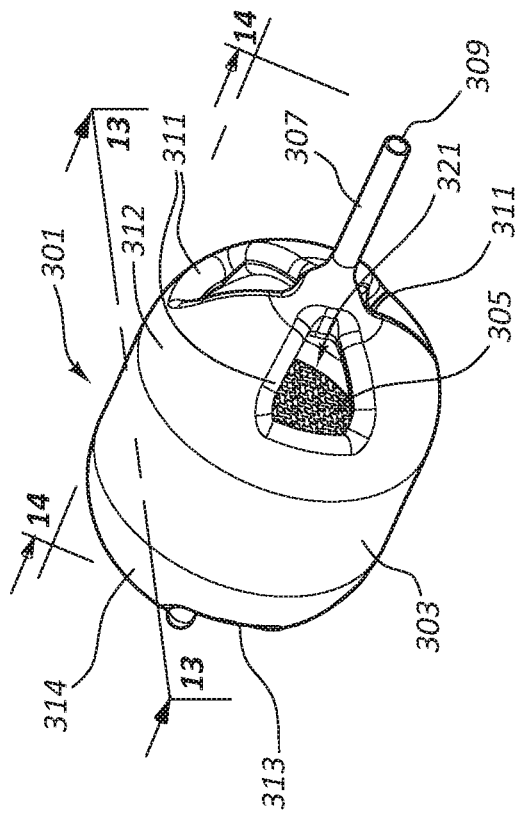
FIG. 12 is a distal end view of the embolic filter balloon of FIG. 9.
Figure 13:
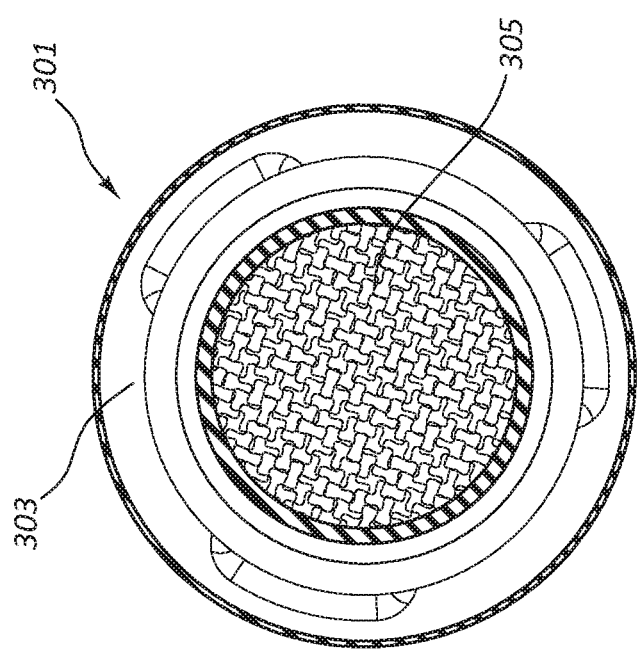
FIG. 13 is a cross-sectional view of the embolic filter balloon of FIG. 10 taken through lines 13-13.

FIG. 12 is a distal end 314 view of the embolic filter balloon 301 of FIG. 9, and FIG. 13 is a cross-sectional view of the embolic filter balloon 301 of FIG. 10 taken through lines 13-13. In some embodiments, the inflatable balloon portion 303 may be substantially cylindrical. Further, the embolic filter balloon 301 may comprise the filter member 305 coupled to the inflatable balloon portion 303 at a position within, or adjacent to, the interior diameter of the inflatable balloon portion 303. Distal openings 313 may allow fluid to flow through the interior diameter of the inflatable balloon portion 303. When at least partially inflated, the inflatable balloon portion 303 may substantially conform to the interior diameter of a body lumen. Such a configuration may direct or result in at least a portion of a fluid flowing through a body lumen to flow or pass through the filter member 305. In some instances, substantially all particles greater than a predetermined size may be captured or filtered by the filter member 305 from the fluid in the body lumen.

As previously described, the filter member 305 may capture particles larger than a predetermined size from the fluid and may allow the fluid to flow through the body lumen while controlling or limiting the flow of particles through the body lumen. In another embodiment, the filter member 305 may be configured to allow passage only of particles smaller than a predetermined size in a fluid of a body lumen.

As described for other embodiments, in the embodiment of FIGS. 9-15, at least one of the inflatable balloon portion 303 and the filter member 305 may comprise a single layer. In another embodiment, at least one of the inflatable balloon portion 303 and the filter member 305 may comprise a plurality of layers. The various characteristics of multilayered balloon constructs, as described above for other embodiments, may similarly apply to this embodiment.

Figure 14:
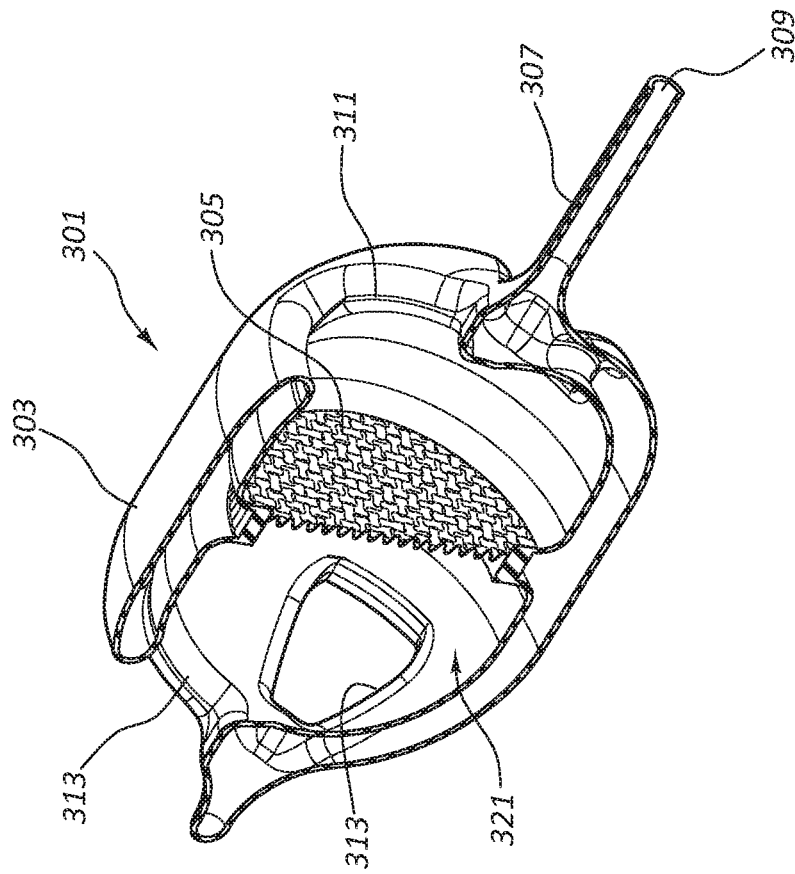
FIG. 14 is a cross-sectional perspective view of the embolic filter balloon of FIG. 10 taken through lines 14-14.

FIG. 14 is a cross-sectional perspective view of the embolic filter balloon 301 of FIG. 10 taken through lines 14-14. In the illustrated embodiment, the filter member 305 may be positioned in an interior fluid flow path 321 of the inflatable balloon portion 303 at a position between the proximal openings 311 and the distal openings 313 of the inflatable balloon portion 303. The inflatable balloon portion 303 and the filter member 305 may be formed of the same material. Alternatively, the inflatable balloon portion 303 may be formed of a different material than the filter member 305. Additionally, the catheter portion 307, comprising the inflation lumen 309, may be formed of the same material as the inflatable balloon portion 303 and/or the filter member 305. Alternatively, the catheter portion 307 may be formed of a different material than the inflatable balloon portion 303 and/or the filter member 305. In embodiments, the filter member 305 may comprise a porous material, a mesh, a woven material, or so forth. The filter member 305 may be coupled to the inflatable balloon member 303, for example, by adhesive, bonding, heat bonding, stitching, and other analogous methods.

Figure 15:
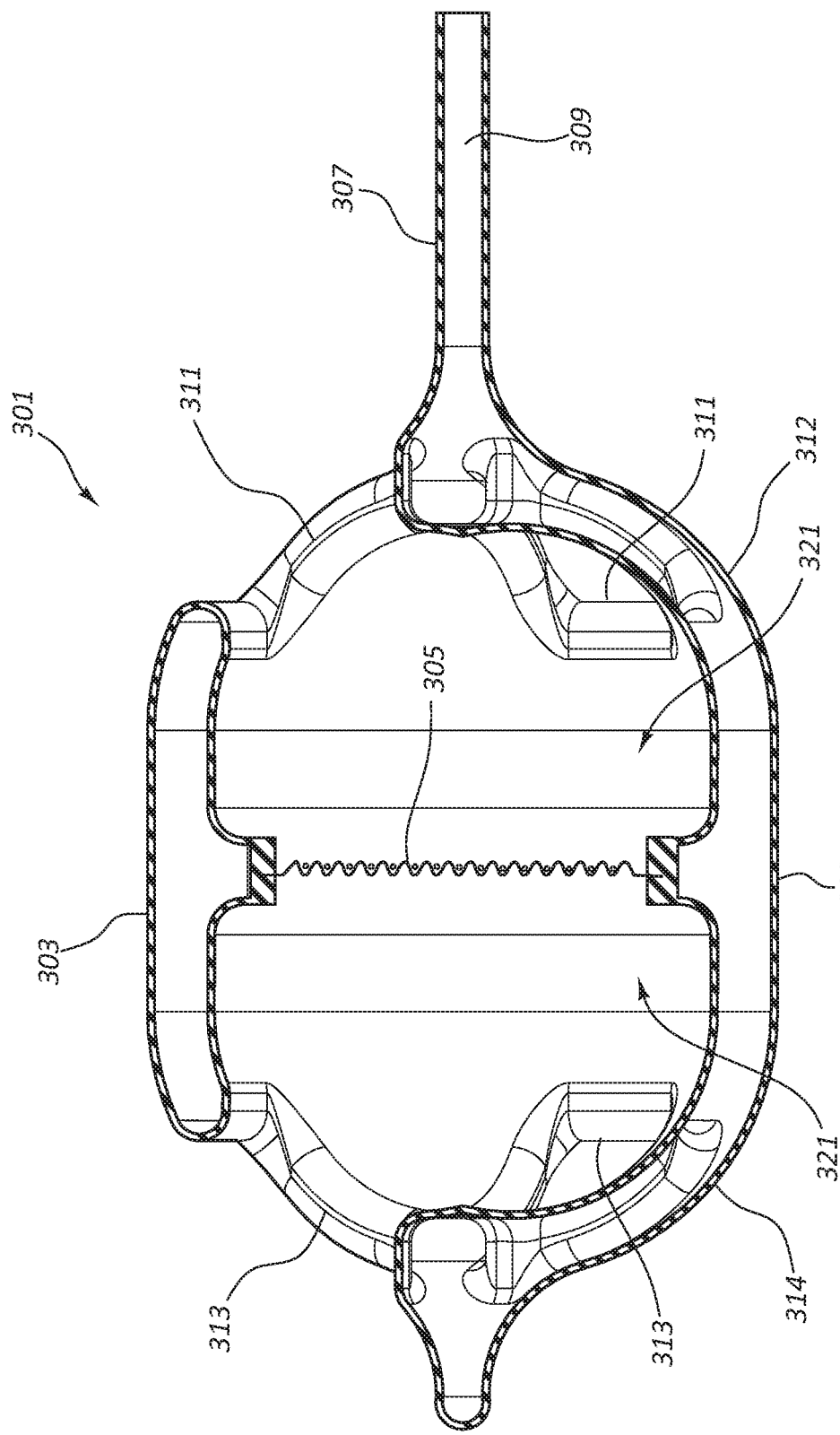
FIG. 15 is a cross-sectional view of the embolic filter balloon of FIG. 12 taken through lines 15-15.

FIG. 15 is a cross-sectional view of the embolic filter balloon 301 of FIG. 12 taken through lines 15-15. As illustrated, the filter member 305 extends across the internal fluid flow path 321 at a position between the proximal 311 and the distal 313 openings of the inflatable balloon portion 303. Further, as illustrated, the catheter portion 307 may comprise the inflation lumen 309 in fluid communication with the inflatable balloon portion 303. As described above, the inflation lumen 309 may be configured to deliver an inflation fluid from an inflation device to the inflatable balloon portion 303 to at least partially inflate the inflatable balloon portion 303. The inflation lumen 309 may also be configured to remove an inflation fluid from the inflatable balloon portion 303 to at least partially deflate the inflatable balloon portion 303. In embodiments, the degree of inflation or deflation of the inflatable balloon portion 303 may be controlled by increasing or decreasing the amount of an inflation fluid flowing into or out of the inflatable balloon portion 303. In other embodiments, the rate of inflation or deflation of the inflatable balloon portion 303 may be controlled by increasing or decreasing the flow rate of an inflation fluid into or out of the inflatable balloon portion 303.

In another embodiment, an inflation lumen, like the inflation lumen 309, may extend through an inflatable balloon portion, like the inflatable balloon portion 303, and may be in at least partial fluid communication with a distal end, like the distal end 314, of the inflatable balloon portion. A catheter portion, like the catheter portion 307, may also comprise a plurality of catheter lumens. For example, the catheter portion may comprise a double-D lumen catheter. In embodiments, the catheter portion may comprise a first lumen comprising an inflation lumen in fluid communication with the inflatable balloon portion. The catheter portion may also extend through the inflatable balloon portion and further comprise a second lumen comprising, for example, a delivery lumen configured to provide a sleeve or sheath for delivery of a medical appliance to a position in a body lumen distal to the inflatable balloon portion. In another example, the first catheter lumen may comprise an inflation lumen in fluid communication with the inflatable balloon portion, and the second catheter lumen may comprise, for example, a delivery lumen configured to provide a sleeve or sheath for delivery of a medical appliance to a position proximal to the embolic filter balloon.

In yet another example, the catheter portion may comprise more than two lumens wherein a first lumen is in fluid communication with the inflatable balloon portion, a second lumen comprises a delivery lumen configured to provide a sleeve or sheath for delivery of a medical appliance or appliances to a position distal to and/or proximal to the embolic filter balloon, a third lumen comprises a delivery lumen configured to provide a sleeve or sheath for delivery of a medical appliance or appliances to a position distal to and/or proximal to the embolic filter balloon, and so forth. In some embodiments, the lumens may comprise inflation lumens, delivery lumens, or other varieties of lumens. In additional embodiments, the number of lumens may correspond to the number of medical appliances coupled to or delivered through the catheter portion. As described above, medical appliances in these and other embodiments herein disclosed comprise, but are not limited to: balloons, catheters, embolic delivery devices, filters, guide wires, introducers, retrieval devices, snares, and stents.

Any of the embodiments disclosed above may be used in connection with a variety of procedures and/or uses. FIGS. 16A-16E illustrate one potential use of the embodiment of the embolic filter balloon 101 of FIGS. 1-7. The use illustrated in FIGS. 16A-16E may also use the embodiment of the embolic filter balloon 301 of FIGS. 9-15. The labeled components of the embodiment of an embolic filter balloon of FIGS. 16A-16E are substantially similar to the labeled components of the embodiment of the embolic filter balloon 101 of FIGS. 1-7 unless otherwise noted. Moreover, as described above, specific features of the embolic filter balloon and related components shown in FIGS. 16A-16E may not be shown or identified by a reference numeral in the drawings and/or specifically discussed in the written description that follows. However, such features may clearly be the same, or substantially the same, as features depicted in other embodiments and/or described with respect to such embodiments. Accordingly, the relevant descriptions of such features apply equally to the features of the embolic filter balloon and related components of FIGS. 16A-16E. Any suitable combination of the features, and variations of the same, described with respect to the embolic filter balloon and components illustrated in FIGS. 1-7, can be employed with the embolic filter balloon and components of FIG. 16A-16E, and vice versa. As previously stated, this pattern of disclosure applies equally to further embodiments described hereafter.

Referring to FIG. 16A, the embolic filter balloon 101 may first be disposed in a vessel 117. In some procedures, a practitioner may select an entry site on an exterior surface of a patient. The entry site, for example, may be adjacent to a radial artery, a femoral artery, or another suitable vessel. At the entry site, the practitioner may use a needle, trochar, or other vesicular access appliance to access a lumen of the vessel 117. The practitioner may then dispose an introducer sheath 125 or other delivery appliance into the vessel 117. The practitioner may also dispose one or more of a catheter, dilator, guide wire, or other relevant appliance into the vessel 117 via the introducer sheath 125 at the entry site. In some instances, the practitioner may advance one or more of the catheter, dilator, guide wire, or other relevant appliance to a site proximal to a treatment site. The practitioner may then utilize one or more of the catheter, dilator, guide wire, or other relevant appliance to assist in advancing the introducer sheath 125 to the site proximal to the treatment site. In other instances, the practitioner may advance the introducer sheath 125 through the vessel 117 to the site proximal to the treatment site without the assistance of an appliance such as a catheter, dilator, or guide wire.

The practitioner may also advance the embolic filter balloon 101 and one or more medical appliances via the introducer sheath 125 to the site proximal to the treatment site. In some instances, the practitioner may advance the embolic filter balloon 101 and/or the one or more medical appliances to a site adjacent to or at the treatment site without utilizing an introducer sheath 125. From the site proximal to the treatment site, the practitioner may advance the embolic filter balloon 101 to a site distal to the treatment site, and the practitioner may also advance the one or more medical appliances to the treatment site. In an angioplasty, for example, the one or more medical appliances may include a balloon catheter. During advancement, the embolic filter balloon 101 may be in a delivery or pre-inflated configuration, as illustrated in FIG. 16A. Such a configuration may facilitate advancement of the embolic filter balloon 101 through the vessel 117 or via the introducer sheath 125 to the site distal to the treatment site. A compact, pre-inflated configuration may also facilitate advancement of the embolic filter balloon 101 along a pathway that may be tortuous.

Figure 16C:
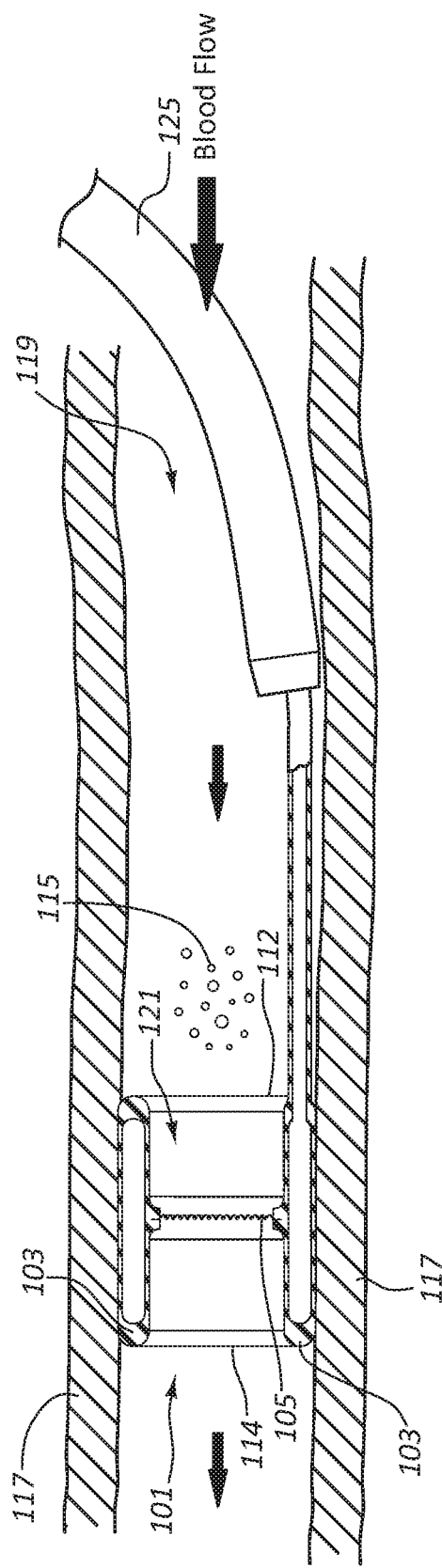
FIG. 16C is a side cross-sectional view of the embolic filter balloon of FIG. 16B, illustrating flow of particles in the blood of a vessel.

Referring now to FIG. 16B, the embolic filter balloon 101 may be at least partially inflated in the vessel 117 at the site distal to the treatment site, such that the inflatable balloon portion 103 at least partially conforms to the inside diameter of the vessel 117. As illustrated in FIGS. 16A-16E, the embolic filter balloon 101 may be disposed in the vessel 117 such that the direction of blood flow, as indicated by arrows, proceeds from a proximal end 112 of the embolic filter balloon 101 to a distal end 114 of the embolic filter balloon 101. Other configurations of the embolic filter balloon 101 within a body lumen are also within the scope of this disclosure. For example, a configuration wherein the direction of blood flow proceeds from a distal end 114 of the embolic filter balloon 101 to proximal end 112 of the embolic filter balloon 101 is also within the scope of this disclosure.

Referring now to FIG. 16C, a plurality of particles 115 may be present in blood 119 flowing through the vessel 117. The particles 115 may be released during a vascular procedure or therapy conducted upstream from the position of the embolic filter balloon 101. For example, during an angioplasty a practitioner may deliver an embolic filter balloon 101 via an introducer sheath 125 to a site distal to a treatment site in a vessel 117. The practitioner may also deliver a balloon catheter through the introducer sheath 125 to the treatment site. At the treatment site, the practitioner may deploy or inflate the balloon catheter. As the balloon catheter inflates, an exterior surface of the balloon catheter may press against an interior diameter of the vessel 117 and may also press a plaque deposit against the interior diameter of the vessel 117. During this procedure, particles 115 of plaque or other debris may be dislodged or released into the blood 119. If the released particles 115 or debris remain in the blood 119 the particles 115, as described above, may at least partially occlude blood 119 flow in the vessel 117 or another vessel or vessels downstream of the treatment site and may result in ischemia, myocardial infarction, stroke, and other potentially adverse medical conditions. To substantially avoid such potentially adverse conditions, the practitioner may deploy the embolic filter balloon 101 at the site distal to the treatment site to filter or capture the particles 115 or debris from the blood 119.

Figure 16D:
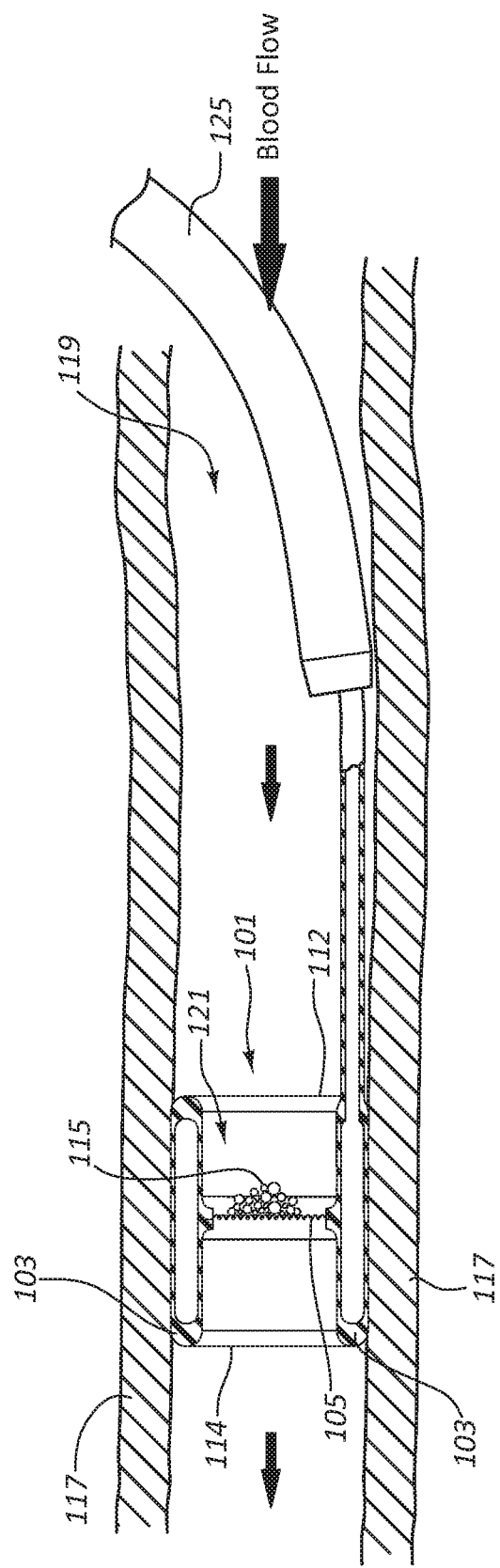
FIG. 16D is a side cross-sectional view of the embolic filter balloon of FIG. 16C, illustrating capture of particles by the embolic filter balloon.

As described above, particles 115 within the scope of this disclosure may comprise biologic and/or synthetic material and may or may not be introduced into the body by the practitioner. For example, some procedures or therapies may include the release of particles 115, including particles 115 of body tissue or other biologic matter, into a fluid in a body lumen. A variety of additional procedures or therapies may also result in the release of particles 115 into a fluid flowing through a body lumen. For example, during expansion of a stent in a body lumen, particles 115 may be dislodged into the fluid in the body lumen. The particles 115, as illustrated in FIG. 16D, may be captured by the filter member 105 as blood 119 flows through the interior flow path 121 of the deployed or inflated embolic filter balloon 101.

Figure 16E:
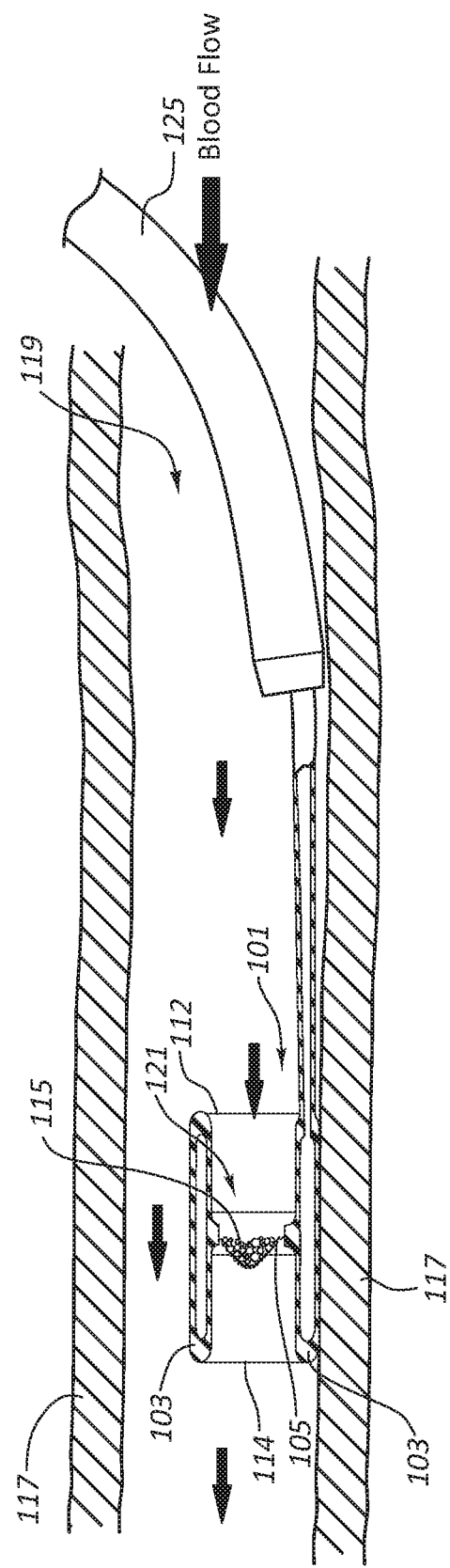
FIG. 16E is a side cross-sectional view of the embolic filter balloon of FIG. 16D, in a partially deflated configuration.

FIG. 16E illustrates that after the particles 115 have been captured by the filter member 105, for example, after an upstream procedure, as described above, releases particles 115 into the blood 119, the embolic filter balloon 101 may be at least partially deflated. Partial deflation of the inflatable balloon portion 103 of the embolic filter balloon 101 may act to secure the captured particles 115 in the embolic filter balloon 101. Deflation of the inflatable balloon portion 103 of the embolic filter balloon 101 may also decrease the size or geometric profile of the embolic filter balloon 101, and may facilitate retrieval of the embolic filter balloon 101 from the vessel 117.

The filter member 105 may be biased to collapse into a basket-like shape upon deflation of the inflatable balloon portion 103. In another embodiment, the filter member 105 may be folded into the delivery configuration in a manner that may provide the filter member 105 with a memory that may prompt the filter member 105 to refold into a similar configuration upon deflation of the embolic filter balloon 101. Such a configuration may keep the particles 115 from escaping from the filter member 105 as the embolic filter balloon 101 is deflated. The embodiment as shown in FIGS. 9-15 may also aid in keeping captured particles, like the particles 115, from escaping from the filter member 305. For example, the rounded distal 314 and proximal 312 ends may aid in maintaining the filter member 305 in a basket-like configuration upon deflation of the embolic filter balloon 301.

In some embodiments, a band or a portion of the embolic filter balloon, like the embolic filter balloon 101, may be coupled to or coated with a radiopaque material. Such a configuration may facilitate imaging of the embolic filter balloon during: delivery of the embolic filter balloon to a target body lumen, use of the embolic filter balloon, and/or retrieval of the embolic filter balloon from a body lumen.

In another example, a practitioner may desire to deliver embolic microspheres to a target vessel in order to intentionally occlude blood flow to a fibroid, tumor, cancer, or other undesirable growth or lesion. The target vessel, however, may branch off from a non-target vessel that the practitioner may desire to avoid occluding with the embolic microspheres. To prevent the embolic microspheres from at least partially occluding the non-target vessel, the practitioner may deploy an embolic filter balloon, like the embolic filter balloon 101, in the lumen of the non-target vessel to filter or capture misdelivered embolic microspheres.

In another procedure for filtering particles, like the particles 115, larger than a predetermined size from a fluid within a body lumen, an embolic filter balloon, like the embolic filter balloon 101, may be introduced into a body lumen. The embolic filter balloon may be at least partially inflated such that a filter member, like the filter member 105, coupled to the embolic filter balloon extends at least partially across the body lumen. The at least partially extended filter member may filter or capture particles larger than a predetermined size from a fluid within a body lumen.

In some procedures or therapies, an additional medical device or devices may be introduced into the body lumen before, during, or after introduction of the embolic filter balloon into the body lumen. As described above, such a medical device or devices may be one or more of the following, but is not limited to: balloons, catheters, embolic delivery devices, filters, guide wires, introducers, retrieval devices, snares, and stents. The filtered particles may comprise particles that are released into the fluid within the body lumen by such a medical device.

An inflatable balloon portion, like the inflatable balloon portion 103, may also be at least partially deflated such that any filtered particles remain trapped in the coupled filter member. Additionally, in some instances, the embolic filter balloon and the filtered particles may be retrieved from the body lumen. In another embodiment, the inflatable balloon portion and the coupled filter member may be detachably coupled to a catheter portion, like catheter portion 107. For example, the inflatable balloon portion and the coupled filter member may remain in a body lumen of a patient and the catheter portion may be retrieved from the patient. In yet another embodiment, the inflatable balloon portion and the coupled filter member may be re-coupled to a catheter portion, like catheter portion 107. For example, a practitioner may detach the inflatable balloon portion and coupled filter member from the catheter portion, and may allow the inflatable balloon portion and coupled filter member to remain in a patient for a period of time. The practitioner may then re-couple the inflatable balloon portion and coupled filter member to a catheter portion, the practitioner may then at least partially deflate the inflatable balloon portion, and the practitioner may retrieve the inflatable balloon portion and coupled filter member from the body lumen of the patient. In some embodiments, at least a portion of the embolic filter balloon may be coated with or coupled to an agent or coating material that may reduce or prevent tissue ingrowth. In such an embodiment, the practitioner may retrieve the embolic filter balloon from the body lumen of the patient without problems associated with tissue ingrowth.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A method of manufacturing an embolic filter balloon, comprising:
   rotationally spinning a flowable material comprising polytetrafluoroethylene (PTFE) to create fibers by rotating a spinneret to expel the flowable material from an orifice on a circumference of the spinneret in the absence of an electric field such that the fibers form an embolic filter; and
   coupling the embolic filter to an inner lumen of the embolic filter balloon.

2. The method of claim 1, wherein rotational spinning comprises:
   mixing a PTFE dispersion with polyethylene oxide (PEO), wherein the PEO is dissolved in water, to form the flowable material.

3. The method of claim 1, wherein the embolic filter of the rotationally spun PTFE fibers has a predetermined porosity to capture particles of a predetermined size.

4. The method of claim 1, further comprising coating the embolic filter with a therapeutic agent.

5. The method of claim 1, further comprising coating the embolic filter with an anti-thrombotic agent.

6. The method of claim 1, further comprising sintering the PTFE fibers.

7. The method of claim 1, wherein the PTFE fibers are micro-fibers.

8. The method of claim 1, wherein the PTFE fibers are nano-fibers.

9. The method of claim 1, wherein the embolic filter is a continuous disc.

10. The method of claim 1, wherein the embolic filter comprises a plurality of layers of PTFE fibers.

11. The method of claim 1, further comprising coating rotational spun PTFE fibers to a substrate of the embolic filter balloon.

12. The method of claim 11, wherein the embolic filter balloon comprises a plurality of layers of PTFE fibers.

13. The method of claim 1, wherein the embolic filter balloon has a proximal end that is shaped to form a dome comprising at least two proximal openings, the proximal end tapering radially inward and in a proximal direction toward a center portion of the proximal end, wherein the center portion is disposed radially inward relative to the at least two proximal openings, wherein the embolic filter balloon has a distal end that is shaped in the form of a dome comprising at least two distal openings, the dome extending distally, and wherein the embolic filter balloon has a cylindrical portion disposed between the proximal end and the distal end.

14. The method of claim 1, wherein the embolic filter balloon is configured to at least partially conform to an inside diameter of a body lumen when the embolic filter balloon is inflated.

15. The method of claim 1, wherein the embolic filter is offset from both a proximal end and a distal end of the embolic filter balloon.

* * * * *